United States Patent
Wakatake et al.

(10) Patent No.: US 8,941,823 B2
(45) Date of Patent: Jan. 27, 2015

(54) SURFACE INSPECTION DEVICE FOR CYLINDRICAL BODY

(75) Inventors: Katsunori Wakatake, Oyama (JP); Hiroyasu Takahashi, Oyama (JP)

(73) Assignee: Showa Denko K.K., Tokyo (JP)

( * ) Notice: Subject to any disclaimer, the term of this patent is extended or adjusted under 35 U.S.C. 154(b) by 243 days.

(21) Appl. No.: 13/376,859

(22) PCT Filed: Jun. 18, 2010

(86) PCT No.: PCT/JP2010/060368
§ 371 (c)(1),
(2), (4) Date: Feb. 3, 2012

(87) PCT Pub. No.: WO2010/150709
PCT Pub. Date: Dec. 29, 2010

(65) Prior Publication Data
US 2012/0127462 A1    May 24, 2012

(30) Foreign Application Priority Data
Jun. 23, 2009 (JP) .................. 2009-148191

(51) Int. Cl.
    *G01N 21/00*     (2006.01)
    *G01N 21/952*    (2006.01)
(52) U.S. Cl.
    CPC .................................. *G01N 21/952* (2013.01)
    USPC .................. 356/237.2; 356/237.1; 356/237.6
(58) Field of Classification Search
    USPC .......................................... 356/237.1–237.6
    See application file for complete search history.

(56) References Cited

U.S. PATENT DOCUMENTS

| | | | |
|---|---|---|---|
| 4,358,202 A * | 11/1982 | Puffer et al. | 356/430 |
| 6,046,803 A * | 4/2000 | Toh | 356/237.2 |
| 7,099,002 B2 * | 8/2006 | Ishiura et al. | 356/237.2 |
| 7,663,745 B2 * | 2/2010 | Zaman et al. | 356/237.2 |
| 7,755,749 B2 * | 7/2010 | Kobayashi et al. | 356/237.1 |
| 8,497,985 B2 * | 7/2013 | Hayashi et al. | 356/237.2 |
| 2002/0196432 A1 * | 12/2002 | Ishiura et al. | 356/237.1 |
| 2004/0165181 A1 * | 8/2004 | Kume et al. | 356/237.2 |

FOREIGN PATENT DOCUMENTS

| JP | 07-140079 A | 6/1995 |
|---|---|---|
| JP | 3054243 B2 | 6/2000 |

(Continued)

OTHER PUBLICATIONS

Official Communication issued in International Patent Application No. PCT/JP2010/060368, mailed on Jul. 13, 2010.

*Primary Examiner* — Tarifur Chowdhury
*Assistant Examiner* — Isiaka Akanbi
(74) *Attorney, Agent, or Firm* — Keating & Bennett, LLP (57) ABSTRACT

A surface inspection device for a cylindrical body includes an illumination light source disposed above the cylindrical body, a beam splitter disposed above the cylindrical body so as to correspond to the illumination light source, and a surface condition recognition device disposed above the beam splitter. Illumination light emitted from the illumination light source is reflected by the beam splitter and applied coaxially to the surface of the cylindrical body, and the reflected light reflected by the surface of the cylindrical body transmits through the beam splitter to be recognized by the surface condition recognition device. The device is configured such that the illumination light from the illumination light source is applied from one end side of the cylindrical body in the axial direction toward, the other end side so as to be in parallel to the axial direction.

9 Claims, 8 Drawing Sheets

(56) References Cited

FOREIGN PATENT DOCUMENTS

| JP | 2001-165868 A | | 6/2001 |
| JP | 2001165868 A | * | 6/2001 |
| JP | 2002-071576 A | | 3/2002 |
| JP | 2006-258726 A | | 9/2006 |
| JP | 2009-031091 A | | 2/2009 |

* cited by examiner

SURFACE INSPECTION DEVICE FOR CYLINDRICAL BODY

TECHNICAL FIELD

The present invention relates to a surface inspection device for a cylindrical body to inspect a surface condition of the cylindrical body and its related technologies.

TECHNICAL BACKGROUND

A cylindrical body such as a photosensitive drum substrate is required to have high surface accuracy, and therefore surface inspection is conducted to screen out cylindrical bodies having surface defects, such as, e.g., scratches, irregularities, adherence of foreign substances, and/or stains.

Figure 8:
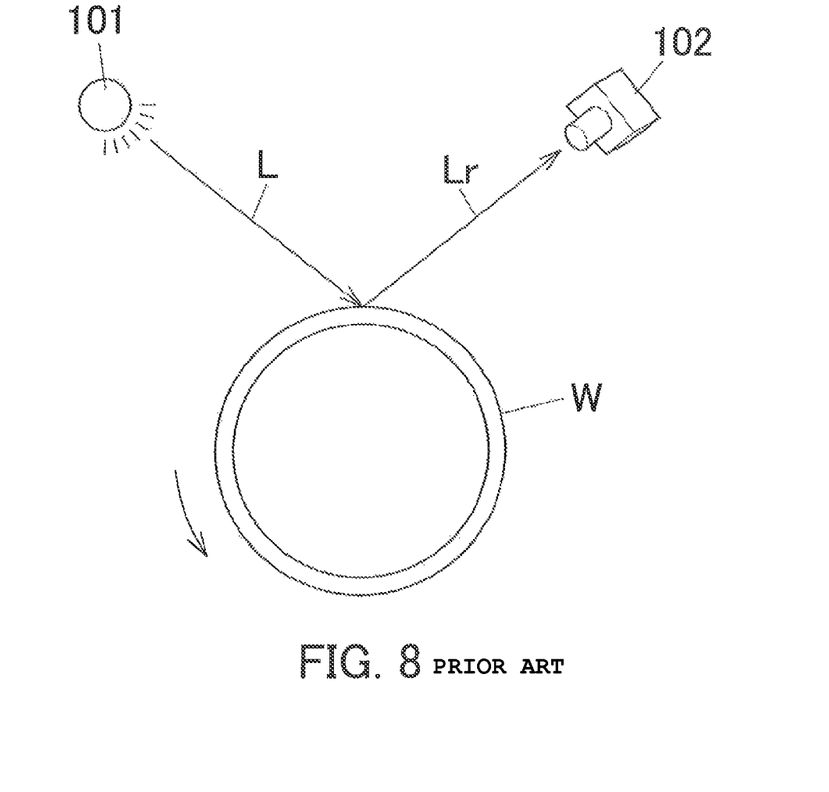
FIG. 8 is a front view schematically showing a conventional surface inspection device for a cylindrical body.

For example, in a surface inspection device for a cylindrical body disclosed in the below listed Patent Document 1, as shown in FIG. 8, it is configured such that illumination light L is irradiated on a cylindrical body W from a light source 101 disposed laterally upward of the cylindrical body W, while the regular reflection light Lr (reflection light image) is captured with a camera 102, so that surface defects of the cylindrical body W are detected based, on the captured image data.

Figure 9:
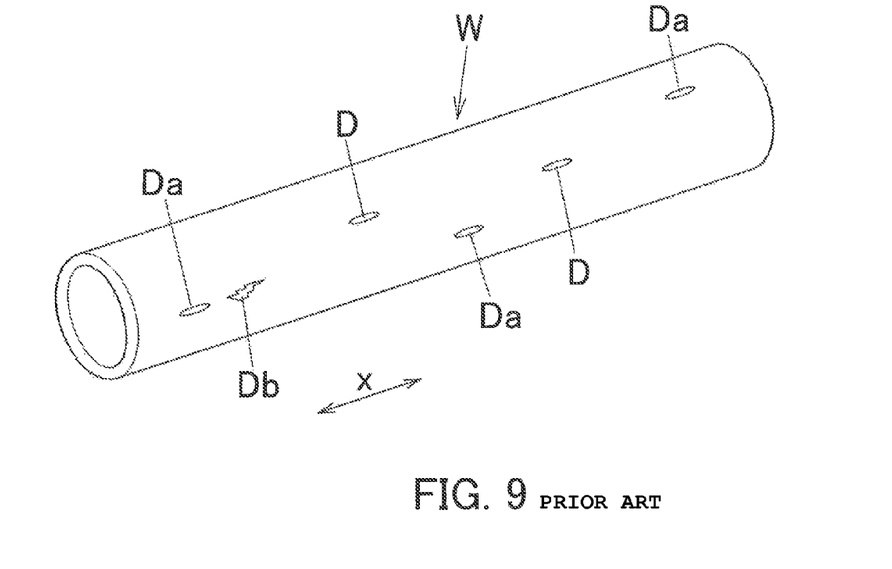
FIG. 9 is a perspective view exaggeratingly showing streak-like concave portions occurred on a surface of a cylindrical body.

In recent years, as a photosensitive drum substrate constituting a cylindrical body W to be inspected, a substrate obtained by drawing an extruded tube has been widely used. As shown in FIG. 9, in a cylindrical body W obtained by drawing, portions that could become defective such, as irregularities on a surface, in most cases, are formed into streak-like shapes extending parallel to the axial direction (longitudinal direction) X. Among these streak-like concave portions D and/or protruding portions, a comparatively shallow streak-like concave portion Da will not become defective, while a steak-like concave portion Db relatively deep in depth or having a standing edge at the circumference thereof will become defective. Thus, in cases where there exist such defective streak-like concave portions Db, the substrate is treated as a defective one,

PRIOR ART DOCUMENTS

Patent Documents

Patent Document 1: Japanese Unexamined Laid-open Patent Application Publication No, H7-140079 (JP-07-140073-A)

Patent Document 2: Japanese Unexamined Laid-open Patent Application Publication No. 2002-71576 (JP-2002-71576-A)

SUMMARY OF THE INVENTION

Problems to be Solved by the Invention

In the conventional surface inspection device for a cylindrical body shown in Patent Document 1, however, the inspection device cannot accurately differentiate between a non-defective streak-like concave portion Da which will not become defective and a defective streak-like concave portion Db which, will become defective, as will be explained below. For example, the inspection device detects all of streak-like irregularities including, e.g., streak-like concave portions D formed on the surface of the cylindrical body, resulting in deteriorated inspection accuracy.

Figure 10:
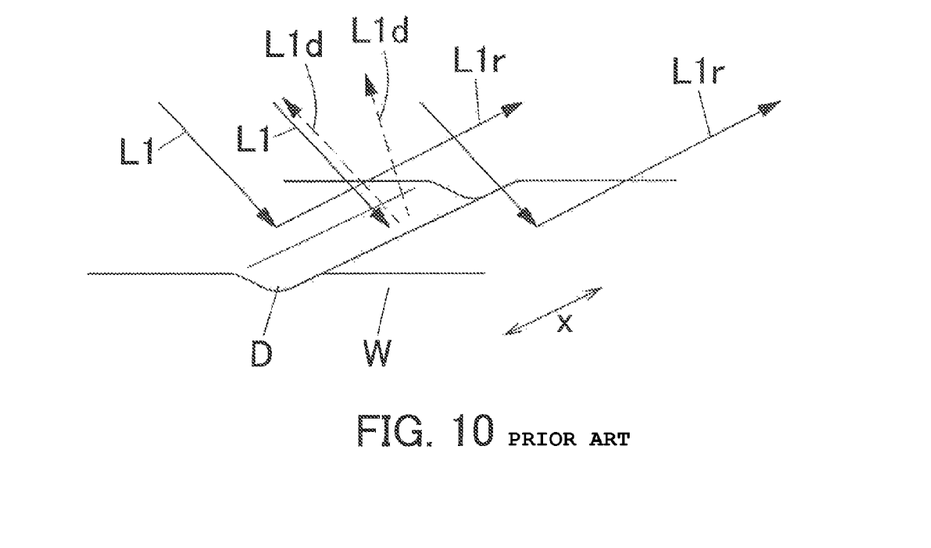
FIG. 10 is a perspective view for explaining a reflection state of illumination light at a periphery of a streak-like concave portion in a conventional surface inspection device.

As show in FIG. 10, according to the conventional surface inspection device for a cylindrical body, in an area of the surface of the cylindrical body not including irregularities such as concave portions B, the illumination light L emitted from the light source 101 is reflected by the surface of the cylindrical body, and the regular reflection light Lr is taken into the camera 102. On the other hand, in the area including, e.g., concave portions D, the illumination light L is diffusely reflected by the inner side surface of the concave portion D and the diffused reflection light Ld is not received by the camera 102. Because the concave portion D is detected based on the difference in the amount of the regular reflection light Lr, all of the concave portions D are detected even if the depth and/or shape of the concave portions D are slightly different from each other. As a result, the device fails to accurately differentiate between non-defective concave portions Da and defective concave portions Db, resulting in deteriorated inspection accuracy.

Preferred embodiments of the present invention were made in view of the aforementioned technical background and/or other problems. The preferred embodiments of the present invention can significantly improve the existing methods and/or devices.

The present invention was made in view of the aforementioned problems, and aims to provide a surface inspection device for a cylindrical body capable of accurately detecting only defective streak-like irregularities which become defective among streak-like irregularities and high in inspection accuracy, and also aims to provide its related technologies.

Other purposes and advantages of the present invention will become apparent from the following preferred embodiments.

In the meantime, a surface inspection method using a coaxial epi-illumination as shown in the above-listed Patent Document 2 is well known as a method for conducting a surface inspection using reflection light. In this surface inspection method, surface defects are detected by coaxially illuminating the surface of the object to be inspected by illumination light and recognizing the reflection light image with a camera. In this inspection method, the surface condition, can be accurately inspected since the surface condition is detected by the image of the regular reflection light reflected perpendicularly with respect to the surface to be inspected.

Figure 5:
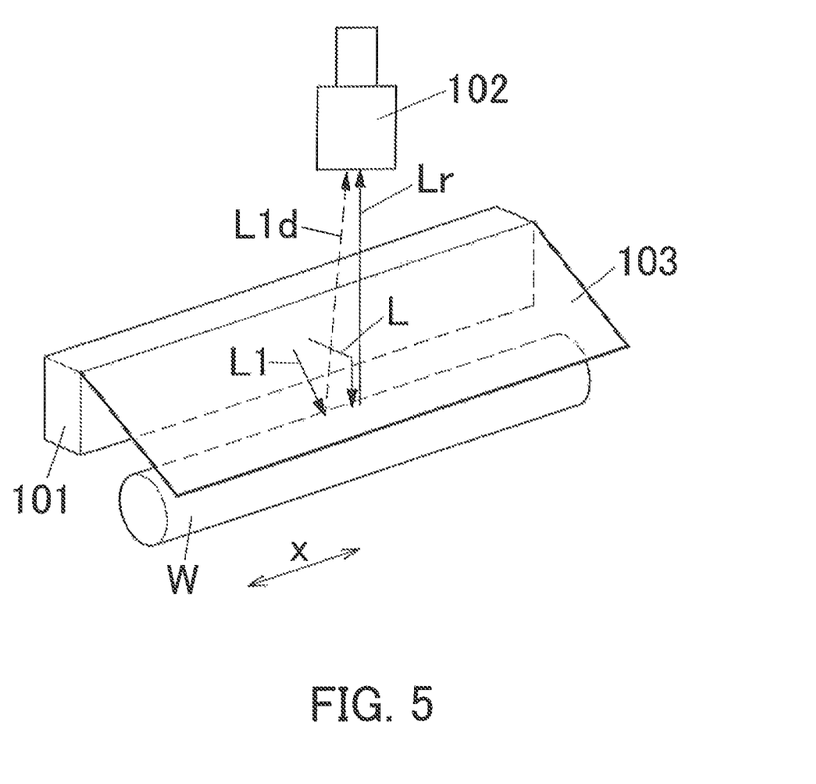
FIG. 5 is a perspective view schematically showing a surface inspection device for a cylindrical body which is a previously proposed technology.
Figure 6:
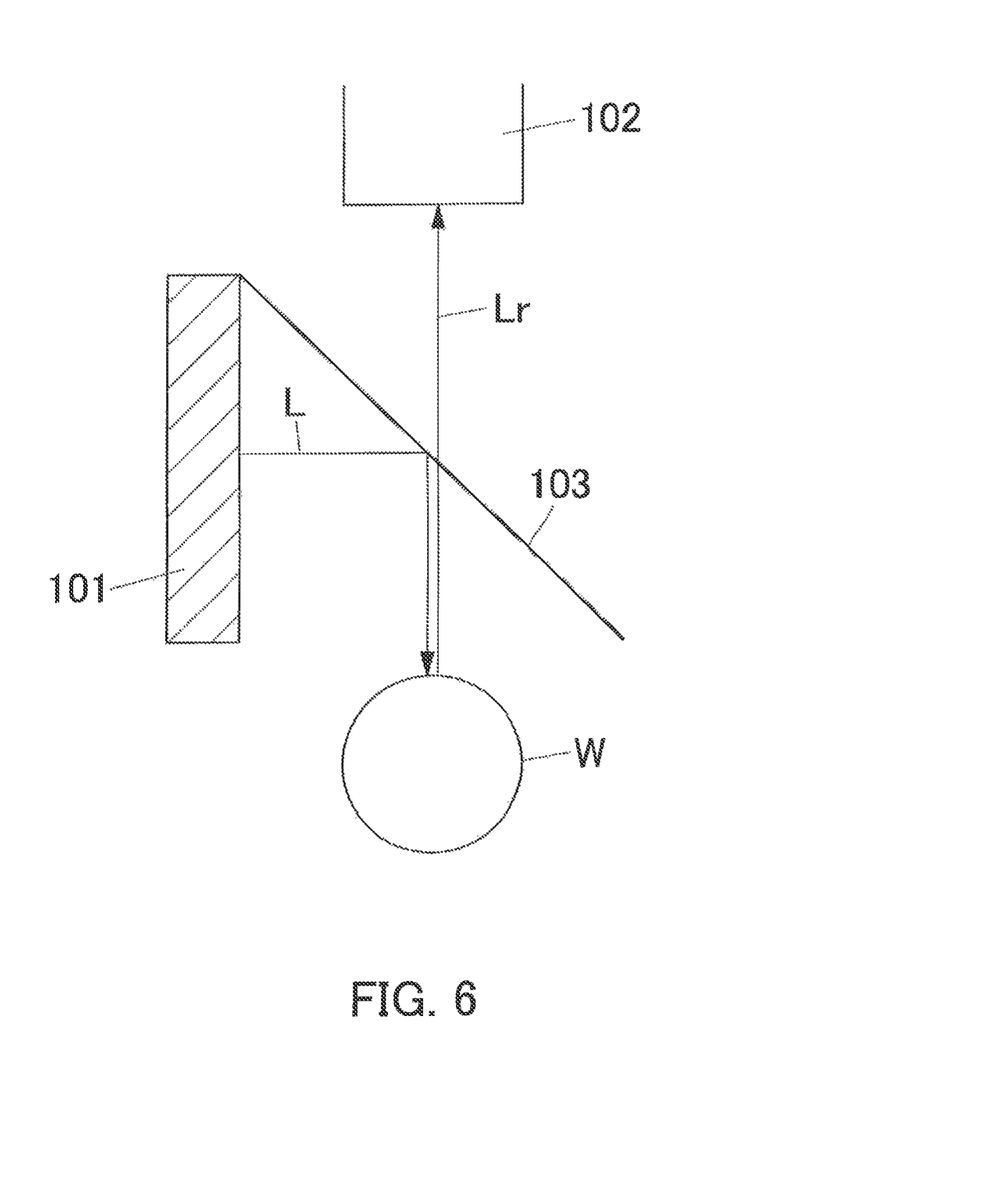
FIG. 6 is a front view schematically showing the surface inspection device of the previously proposed technology.

Therefore, the inventor has proposed a method for conducting a surface inspection for a cylindrical body using such coaxial epi-illumination. In detail, as shown in FIGS. 5 and 6, a light source 101 is disposed laterally upward of the cylindrical body W, a half mirror 103 is arranged above, the cylindrical body W, and a camera 102 is arranged above the half mirror 103. Thus, the illumination light L emitted from the light source 101 is reflected by the half mirror 103, and the reflected illumination light L is coaxially applied to the cylindrical body W perpendicularly from the above. The illumination light L is reflected, perpendicularly upward by the surface of the cylindrical body W, and the reflected light Lr is transmitted through the half mirror 103 and received by the camera 102.

Figure 4A:
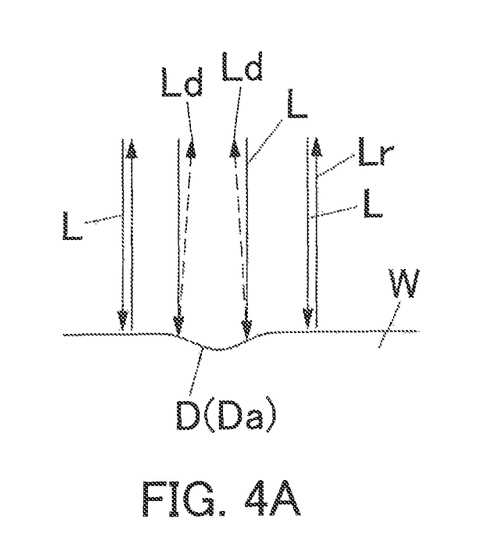
FIG. 4A is a front view for explaining a reflection state of a coaxial epi-illumination light at the periphery of the non-defective streak-like concave portion.
Figure 4B:
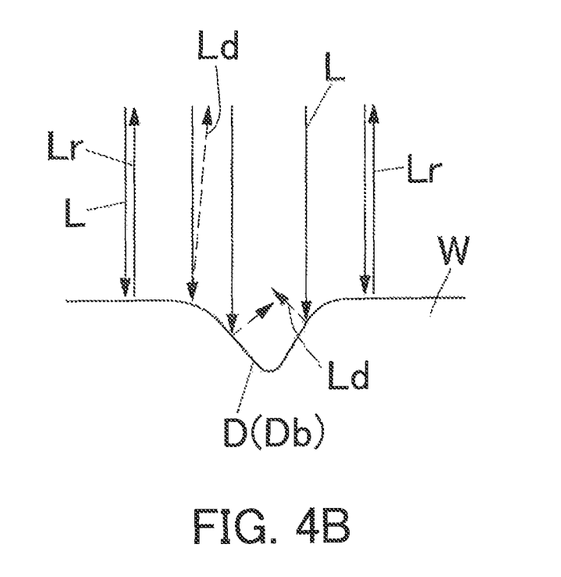
FIG. 4B is a front view for explaining the reflection state of the coaxial epi-illumination light at the periphery of the defective streak-like concave portion.

As shown in FIG. 4A, according to this inspection method, in an area including a shallow streak-like concave portion D, i.e., a non-defective streak-like concave portion Da, there is less diffused reflection lights Ld that deviate from the optical axis of the camera 102. On the other hand, as shown in FIG. 4B, in an area including a deep streak-like concave portion D, i.e., a defective streak-like concave portion Db, there is more, diffused reflection lights Ld that deviate from the optical axis of the camera 102. Consequently, the non-defective streak-like concave portion Da and the defective streak-like concave portion Db can be differentiated by the difference in the amount of light received by the camera 102, and among the streak-like concave portions D, only the defective ones can be accurately detected.

However, as the applicant continuously conducts thorough experiments and research, it became apparent that it is difficult to assuredly achieve high inspection accuracy even, with the proposed technology.

Figure 7:
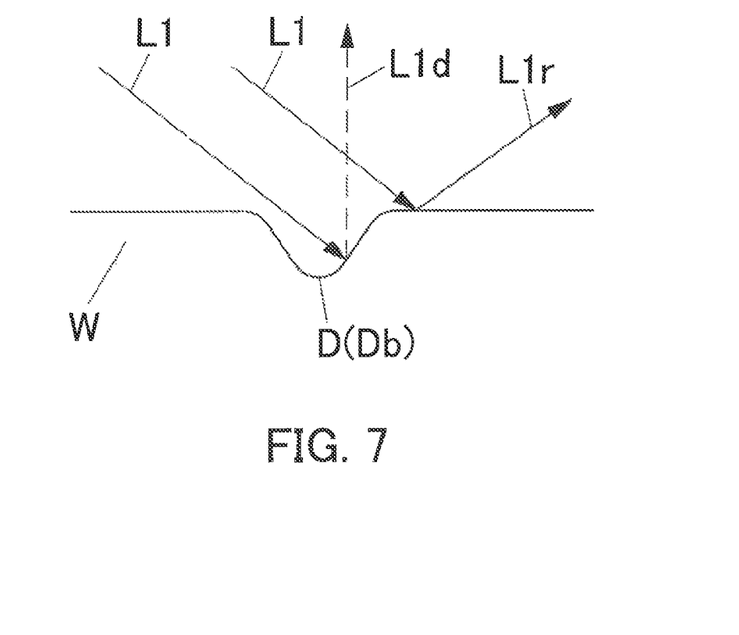
FIG. 7 is a perspective view for explaining a reflection state of direct illumination light at the periphery of the defective streak-like concave portion in the surface detection device of the previously proposed technology.

In other words, as shown in FIG. 7, in the surface inspection, device for a cylindrical body according to the aforementioned proposed technology, since the illumination light L is emitted from the illumination source 101 from the side of the cylindrical body W, that is, horizontally in a direction perpendicular to the axial direction X of the cylindrical body W in a plan view, among the illumination lights L emitted from the light source 101, the illumination light L1 that directly reaches the cylindrical body W is emitted in a direction perpendicular to the defective streak-like concave portion Db. Therefore, the direct illumination light L1 is diffusely reflected by the inner side surface of the defective streak-like concave portion Db, and a portion of the diffused reflection light L1$d$ is received by the camera 102. In this way, unnecessary diffused, reflection light L1$d$ is recognized by the camera 102 even in the area of the defective streak-like concave portion Db, and in some cases, the defective streak-like concave portion Db is falsely detected as a normal area. Thus, it became apparent that it is difficult to assuredly solve the problem that the accuracy of the inspection decreases.

The above explanation was made while exemplifying a streak-like concave portion, but it should be noted that, in the case of a streak-like protruding portion, unnecessary diffused reflection light is also recognised by the camera 102, resulting in deteriorated inspection accuracy, Means to Solve the Problems To solve the aforementioned problems, the present invention is provided with the following means,

[1] A surface inspection device for a cylindrical body provided with an illumination light source disposed above the cylindrical body, a beam splitter disposed above the cylindrical body so as to correspond to the illumination light source, and a surface condition recognition means disposed above the beam splitter, wherein illumination light emitted from the illumination light source is reflected by the beam splitter and applied coaxially to a surface of the cylindrical body, and reflected light reflected by the surface of the cylindrical body transmits through the beam splitter to be recognized by the surface condition recognition means, characterized in that the surface inspection device is configured such that the illumination light from the illumination light source is applied from one end side of the cylindrical body in the axial direction toward the other end side so as to be in parallel to the axial direction.

[2] The surface inspection device for a cylindrical body as recited in the aforementioned item 1, wherein the beam splitter is arranged at at least a part of the cylindrical body in the axial direction so that the illumination light reflected by the beam splitter is applied to a part of the cylindrical body in the axial direction.

[3] The surface inspection device for a cylindrical body as recited in the aforementioned item 1 or 2, wherein the beam splitter is constituted by a half mirror.

[4] The surface inspection device for a cylindrical body as recited in any one of the aforementioned items 1 to 3, wherein the cylindrical body is an aluminum or aluminum alloy drawn tube obtained through a drawing process.

[5] The surface inspection device for a cylindrical body as recited in any one of the aforementioned items 1 to 4, wherein the cylindrical body is a photosensitive drum substrate.

[6] A surface inspection method for a cylindrical body in which illumination light emitted from an illumination light source is reflected by the beam splitter and applied coaxially to a surface of the cylindrical body, and reflected light reflected by the surface of the cylindrical body transmits through the beam splitter to be recognized by the surface condition recognition means, wherein the method is configured such that the illumination light from the illumination light source is applied from one end side of the cylindrical body in the axial direction toward the other end side so as to be in parallel to the axial direction.

[7] A coaxial epi-illumination device used for a surface inspection device for a cylindrical body for inspecting a surface condition of the cylindrical body on the reflected light reflected by a surface of the cylindrical body, comprising:

an illumination light source disposed above the cylindrical body; and a beam splitter disposed above the cylindrical body so as to correspond, to the illumination light, source so that illumination light emitted from the illumination light source is reflected by the beam splitter and applied coaxially to a surface of the cylindrical body, and reflected light reflected by the surface of the cylindrical body transmits through the beam splitter, wherein the coaxial epi-illumination device is configured such that the illumination light from the illumination light source is applied, from one end side of the cylindrical body in the axial direction toward the other end side so as to be in parallel to the axial, direction.

In the columns of "CLAIMS" and "MEANS TO SOLVE THE PROBLEMS" of this application, the expression "above" is used to mean a direction perpendicular to the axial direction of the cylindrical body, or a radially outward, and does not refer to a direction defined with reference to the gravitational direction.

However, in the column of "EMBODIMENTS FOR CARRYING OUT THE INVENTION", the directions are explained based on the gravitational direction, and the expression "above" is used to mean an upper side in the vertical direction.

Effect of the Invention

According to the surface inspection device of the cylindrical body of Invention [1], since the condition of the surface of the cylindrical body is recognized, by the reflection light image of the coaxial epi-illumination light, the surface condition can be accurately grasped, which enables to improve, the inspection accuracy. Furthermore, since the illumination light is emitted along the axial direction from one end side of the cylindrical body, even if there exist streak-like irregularities extending along the axial direction, the reflected light of the direct illumination light directly emitted on the surface of the cylindrical body can be prevented from being unnecessary received by the surface condition recognition means, which enables to maintain the high accuracy of inspection.

According to the surface inspection device for a cylindrical body of Invention [2], the illumination light source and beam splitter can be reduced in size, which in turn can reduce the size of the inspection device.

According to the surface inspection device for a cylindrical body of Invention [3], the inspection accuracy can be more assuredly improved.

According to the surface inspection device for a cylindrical body of Inventions [4] and [5], the aforementioned effects can be obtained more assuredly because the object to be inspected is suited for the inspection device.

According to the surface inspection method for a cylindrical body of Invention [6], the same functions and effects can be obtained in the same manner as mentioned above.

According to the coaxial epi-illumination device for use in the surface inspection device for a cylindrical body of Invention [7], the same functions and effects can be obtained in the same manner as mentioned above.

EMBODIMENTS FOR CARRYING OUT THE INVENTION

Figure 1:
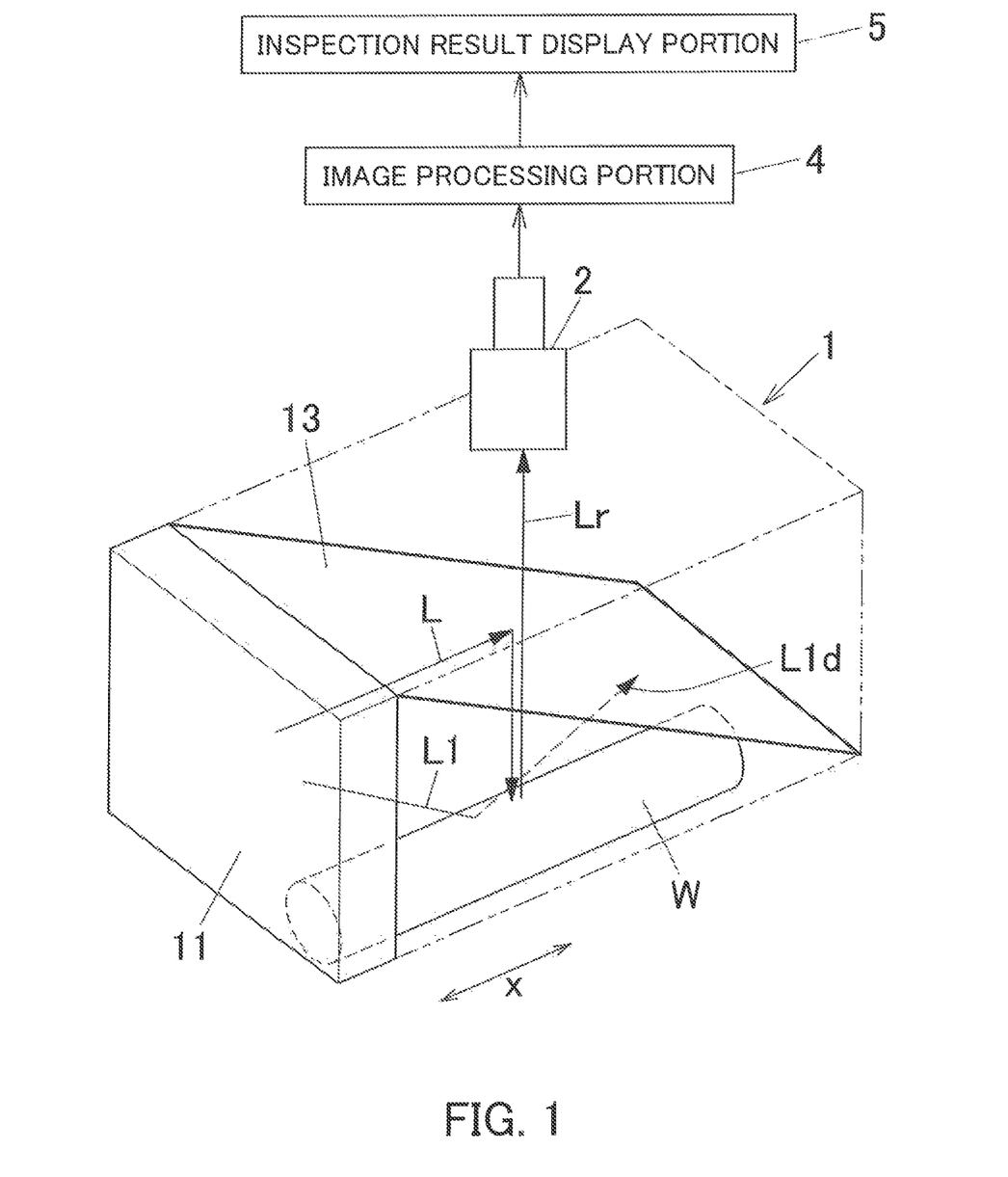
FIG. 1 is a perspective view schematically showing a surface inspection device for a cylindrical body according to an embodiment of the present invention.
Figure 2:
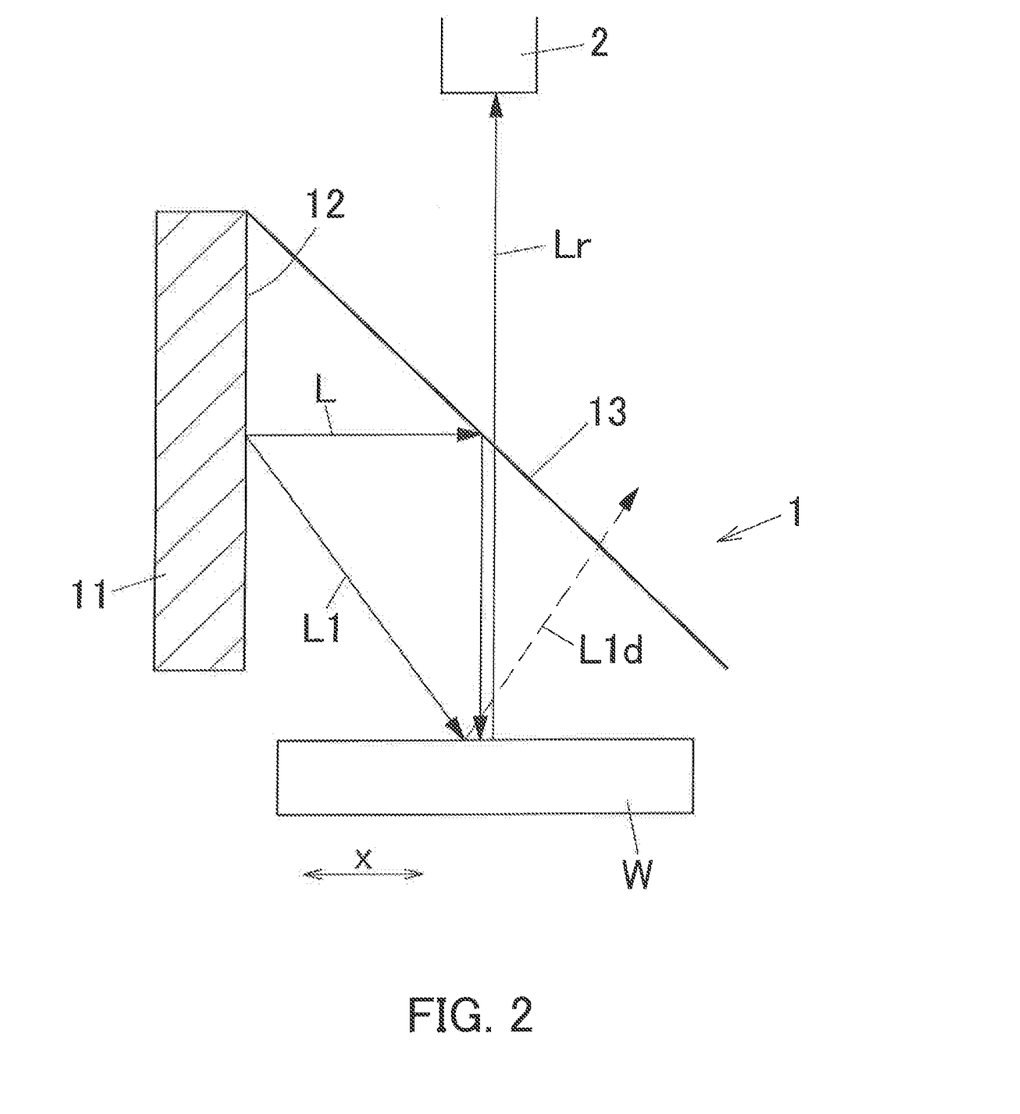
FIG. 2 is a side view schematically showing the surface inspection device of the embodiment.

FIGS. 1 and 2 are drawings showing a surface inspection device for a cylindrical body according to an embodiment of the present invention. As shown in both figures, this surface inspection device is configured to inspect a surface of a cylindrical body W as an object to be inspected (work).

The cylindrical body W is used as, for example, a photosensitive drum, a transferring roller, a developing roller and other parts of a copying machine constituting an electrophotography system, a printer, a facsimile, and their complex machine.

Among cylindrical bodies W capable of constituting these members, a cylindrical body W used for an element tube or a substrate for a photosensitive drum for use in, e.g., a copying machine and a printer using an electrophotography system can be exemplified as a preferable example in the embodiment. The photosensitive drum substrate will be referred to as a tubular member after subjected to cutting, drawing, etc., but before forming a photosensitive layer thereon. Also, a tubular member after forming a photosensitive layer on a photosensitive drum substrate can be constituted as a cylindrical body W to be inspected in the present invention.

As a production method for the cylindrical body W, a combination of an extrusion method and a drawing method can be exemplified. Needless to say, in the present invention, the production method for the cylindrical body W is not limited to the above, and any method, such as, e.g., extruding, drawing, forging, casting, injection molding, and cutting, or a combination thereof, can be employed so long as the method can produce a tubular member.

Further, the material for the cylindrical body W is not specifically limited, and a variety of metal materials and synthetic resins can be used. For example, aluminum and aluminum alloys (1000 to 7000 series), copper and copper alloys, steel, and magnesium and magnesium alloys, can be exemplified. Among them, a cylindrical body W made of aluminum alloy is suited to be inspected for the present invention.

The surface inspection device of this embodiment is provided with a coaxial epi-illumination device 1 disposed above the cylindrical, body W and a camera 2 disposed above the coaxial epi-illumination device 1 as basic components.

The coaxial epi-illumination device 1 is provided with an illumination light source 11 disposed above and outside of one end of the cylindrical body W in the axial, direction X, and a half mirror 13 disposed above the cylindrical body W so as to correspond to the illumination light source 11 and constituting a beam splitter.

The illumination light source 11 is arranged in a state in which the light emitting surface 12 faces toward the other end of the cylindrical body, and the illumination light L emitted from the light emitting surface 12 is projected from a position above one end side of the cylindrical body W to the half mirror 13 toward the other end in parallel to the axial direction X of the cylindrical body W.

The half mirror 13 is arranged above the cylindrical body W so as to cover the entire, area of the cylindrical body W in the axial direction thereof at an inclined angle of 45° (degrees) with the one end side positioned higher and the other end positioned lower.

The illumination light L emitted from the illumination light source 11 toward the half mirror 13 is reflected by the half mirror 13 and applied to the cylindrical body surface from perpendicularly above, and the illumination light L applied to the cylindrical body surface is reflected perpendicularly upward by the cylindrical body surface, and the reflected light Lr transmits through the half mirror 13.

In this embodiment, the illumination light source 11 of the coaxial epi-illumination device 1 is constituted by a light emitting means capable of obtaining high brightness, such as, e.g., a plurality of LEDs arranged in line or on a flat surface or a fluorescent lamp.

The camera 2 is disposed at a position perpendicularly above the half mirror 13 so as to face downward. Thus, the reflected light Lr transmitted through the half mirror 13 after being reflected by the cylindrical body surface is received by the camera 2.

In this embodiment, the camera 2 is constituted by, e.g., line sensors in which a number of light quantity detection elements are arranged one-dimensionally along the axial direction X of the cylindrical body W.

In this embodiment, the illumination light L reflected by the half mirror 13 to be applied to the cylindrical body W is a so-called coaxial epi-illumination light in which the optical axis of the illumination light L to be applied to the cylindrical body W coincides with the optical axis of the reflected light Lr (optical axis of the camera 2).

In this embodiment, the camera 2 constitutes the surface condition recognition means. As the surface condition recognition means, a light quantity measurement means for measuring light quantity can also be used.

On the other hand, as shown in FIG. 1, the surface inspection device of this embodiment is provided with an image processing portion 4 for processing the reflected light image taken by the camera 2, and an inspection result, display portion 5, such as, e.g., a liquid crystal display or a CRT display, for displaying the processed image and/or the inspection result determined based on the image.

Furthermore, in the surface inspection device of this embodiment, a rotary driving means (not illustrated) for rotating the set cylindrical body W about, its axis is provided.

In this embodiment, a controller for controlling the operation of the surface inspection device according to predetermined program is provided. The controller is constituted by for example, a microcomputer, and includes image processing program for processing the image data taken by the camera 2. In this embodiment, the image processing program functions as the image processing portion 4.

Further, the controller is configured to detect existence or nonexistence of a defective portion Db by inspecting the surface condition of the cylindrical body W based on the image processed by the image processing portion 4, and to output to display the inspection result and/or the image of the cylindrical body surface such as the defective portion image processed by the image processing on the inspection result display portion 5.

In the surface inspection device of the embodiment constituted as mentioned above, when inspecting the surface condition of the cylindrical body W, an inspection start instruction is given to the controller in a state in which the cylindrical body W is set at a predetermined position. In this way, the cylindrical body W is rotated about the axis and the illumination light source 11 is turned on.

The illumination light L emitted from the illumination light source 11 is projected in parallel to the axial direction X from one end side of the cylindrical body W and reflected perpendicularly downward by the half mirror 13. The illumination light L reflected, by the half mirror 13 is coaxially applied at a right angle to the upper side surface of the cylindrical body W, and reflected, perpendicularly upward by the surface. Furthermore, the reflected light Lr transmits through the half mirror 13 and is received by the camera 2.

The reflected light image of the cylindrical body surface taken by the camera 2 is processed by the image processing portion 4, and based on the processed image, existence or nonexistence of defective portions is inspected. The judgment of existence or nonexistence of defective portions is conducted based on the light quantity of the reflected light Lr obtained by the camera 2.

In detail, among the cylindrical body surface, in a flat area where there exists no concave portion or the like, the regular reflection light Lr of the illumination light L is large in light quantity, resulting in a larger light quantity of the reflected light image. On the other hand, in an area where there exists a concave portion or the like, the diffuse reflection of the illumination light L increases and the mirror reflection decreases, resulting in a smaller light quantity of the reflected light image. Thus, based on the difference in the light quantity, defective portions, such as, e.g., concave portions, are detected.

In this embodiment, among the streak-like concave portions D, a comparatively shallow non-defective streak-like concave portion Da which does not become defective, and a comparatively deep defective streak-like concave portion Db which becomes defective can be clearly differentiated, which enables assured detection of only the defective streak-like concave portion Db. In other words, as shown in FIG. 4A, in the area including a shallow non-defective streak-like concave portion Da, the diffused reflection light Ld of the coaxial epi-illumination light L decreases while the regular reflection light Lr increases. On the other hand, as shown in FIG. 4B, in the area including a deep defective streak-like concave portion Db, the diffused reflection light Ld of the coaxial epi-illumination light L increases while the regular reflection light Lr decreases. Thus, in the reflection light image of the streak-like concave portion D taken by the camera 2, if the light quantity exceeds a predetermined value, the streak-like concave portion is determined to be a non-defective streak-like concave portion Da, and if the light quantity is less than the predetermined value, the streak-like concave portion is determined to be a defective streak-like concave portion Db. In this way, only the defective streak-like concave portion Db can be accurately detected as a defective portion, and the inspection accuracy can be improved.

In addition, the surface inspection device of this embodiment can prevent the reflection light L1d of the direct illumination light L1 from unnecessarily being received by the camera 2, like in the surface inspection device of the previously proposed technology shown, in FIGS. 5 to 7.

In other words, as explained above, in the previously proposed technology shown in FIGS. 5 to 7, when the direct illumination light L1 from the illumination light source 101 is applied to the defective streak-like proposed portion Db on the cylindrical body surface, the direct illumination light L1 is diffusely reflected by the inner-side surface of the defective streak-like conceive portion Db, and a portion of the diffused reflection light L1d is received by the camera 102, which deteriorates the inspection accuracy.

Figure 3:
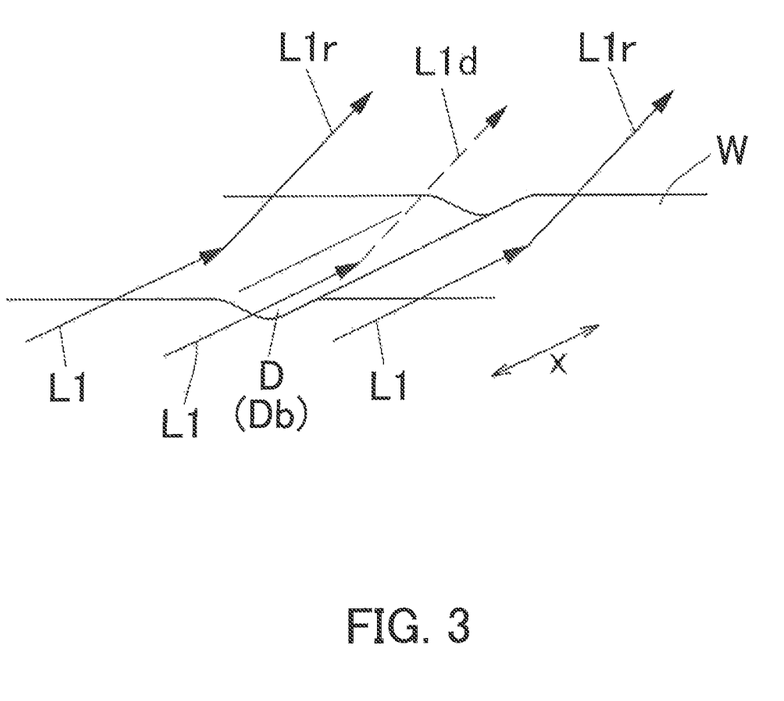
FIG. 3 is a perspective, view for explaining a reflection state of direct illumination light at a periphery of a defective streak-like concave portion in the surface inspection device of the embodiment.

On the other hand, in the surface inspection device of this embodiment, since it is configured such that the illumination light L is emitted along the axial direction X from one end side of the cylindrical body W in the axial direction X, the illumination light L is emitted along the longitudinal direction of the streak-like concave portion D. For this reason, as shown in FIGS. 1 and 3, when the direct illumination light L directly emitted on the cylindrical body surface is applied to the area including streak-like concave portions D such as the defective streak-like concave portions Db, both the regular reflection light L1r and the diffused reflection light. L1d are reflected obliquely upward toward the other end of the cylindrical body W. Therefore, the reflected lights L1r and L1d will not be directed perpendicularly upward. Consequently, the reflection lights L1r and L1d of the direct illumination light L1 can be prevented from being received by the camera 2, and the actual quantity of light received by the camera 2 accurately coincides with the quantify of the reflection light Lr of the coaxially applied illumination light L. As a result, for example, the defective, streak-like concave portion Db can be accurately recognized as a defective portion, which further improves the inspection accuracy.

In the above explanation, it is judged whether the streak-like concave portion D is a defective portion or a non-defective portion. Needless to say, however, the surface inspection device of this embodiment is configured to detect a defective portion other than a streak-like concave portion, such as, e.g., non-steak-like irregularities, scratches, adhesion, of foreign, materials, and stains, based on the reflected light image captured by the camera 2.

As described above, according to the surface inspection device of this embodiment, since the condition of the cylindrical body surface is recognised by the reflected light image of the coaxial epi-illumination light, the surface condition can be accurately assessed, which enables to improve the inspection accuracy.

Furthermore, in this embodiment, since the illumination, light L from the illumination light source 11 is emitted along the axial direction X from one end side of the cylindrical body W, the reflection light of the direct illumination light L1 directly emitted to the cylindrical body surface from the illumination light source 11 will not be unnecessarily received by the camera 2, which in turn can maintain the high detection accuracy.

Also, in the surface inspection device of this embodiment, since it is configured such that the coaxial epi-illumination light L1 is applied at one time to the entire longitudinal area of the cylindrical body W, the entire longitudinal area of the cylindrical body W can be inspected at one time, resulting in improved inspection efficiency.

Further, according to the surface inspection device of this embodiment, since the illumination light is applied parallel to the longitudinal direction of the defect, even if the direct illumination light L is directly applied to the cylindrical body surface from the illumination light source 11, diffused reflection will less likely occur. Accordingly, a large quantity of the diffused reflection light does not enter the camera 2, and therefore it is not required to separately provide an optical means, such as, e.g., an aperture or a parallel beam illumination, to prevent entering of the light. This enables to simplify in structure and reduce in cost.

In the aforementioned embodiment, the explanation was made while exemplifying a streak-like concave portion as a defective portion. However, in the same manner as explained above, even in the case of a steak-like protrusion, a defective high protrusion and a non-defective low protrusion can be assuredly distinguished to accurately detect a defective streak-like protrusion.

In the aforementioned embodiment, using the half mirror disposed to cover the entire longitudinal area of the cylindrical body from one end side of the cylindrical body to the other end side, the illumination light is applied to the entire longitudinal area of the cylindrical body. However, the present invention is not limited to that, and allows to use a half mirror disposed to cover only a part of the longitudinal portion of the cylindrical body to apply the illumination light only to the part of the longitudinal portion of the cylindrical body. In this case, the coaxial epi-illumination light device can be decreased in size, which in turn can reduce the entire size of the surface inspection device.

Furthermore, in the case of using a small coaxial epi-illumination device that illuminates only a part, of a cylindrical body, it can be configured such that the coaxial epi-illumination device is arranged movably in the longitudinal direction of the cylindrical body surface W so that the entire longitudinal area of the cylindrical body W can be inspected while moving the device, and also can be configured such that a plurality of coaxial epi-illumination devices are arranged along the longitudinal direction of the cylindrical body W to inspect the entire longitudinal area of the cylindrical body W at one time.

In the aforementioned embodiment, the explanation was made while exemplifying the case in which optical members such as the illumination light source, the half mirror and the camera are disposed above the cylindrical body disposed horizontally. However, the present invention is not limited to the above. In the present invention, the optical members can be disposed at any positions as long as they are disposed at positions in the radially outward direction perpendicular to the axial direction of the cylindrical body, i.e. they are disposed at the side of the cylindrical body.

The present invention claims priority to Japanese Patent Application No. 2009-143191 filed on Jun. 23, 2009, the entire disclosure of which is incorporated herein by reference in its entirety.

It should be understood that the terms and expressions used herein are used for explanation and have no intention to be used to construe in a limited manner, do not eliminate any equivalents of features shown and mentioned herein, and allow various modifications falling within the claimed scope of the present invention.

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive.

INDUSTRIAL APPLICABILITY

The surface inspection device of the present invention can be used as an inspection device for inspecting a surface, condition of a cylindrical body.

DESCRIPTION OF THE REFERENCE NUMERALS

1 . . . coaxial epi-illumination device
11 . . . illumination light source
13 . . . half mirror (beam splitter)
2 . . . camera (surface condition recognition means)
L: illumination light
Lr: regular reflection light
W: cylindrical body
X: axial direction

The invention claimed is:
1. A surface inspection device for a cylindrical body provided with an illumination light source disposed above the cylindrical body, a beam splitter disposed above the cylindrical body so as to correspond to the illumination light source, and a surface condition recognition device disposed above the beam splitter, wherein illumination light emitted from the illumination light source is reflected by the beam splitter and applied coaxially to a surface of the cylindrical body, reflected light reflected by the surface of the cylindrical body transmits through the beam splitter to be recognized by the surface condition recognition device, and the beam splitter is arranged to extend along an entire longitudinal length of the cylindrical body, wherein the surface inspection device is configured such that the illumination light from the illumination light source is applied from one end side of the cylindrical body in an axial direction of the cylindrical body toward the other end side of the cylindrical body so as to be in parallel to the axial direction, and such that the illumination light is simultaneously applied to the entire longitudinal length of the cylindrical body at one time.

2. The surface inspection device for a cylindrical body as recited in claim 1, wherein the beam splitter is arranged at at least a part of the cylindrical body in the axial direction so that the illumination light reflected by the beam splitter is applied to a part of the cylindrical body in the axial direction.

3. The surface inspection device for a cylindrical body as recited in claim 1, wherein the beam splitter is constituted by a half mirror.

4. The surface inspection device for a cylindrical body as recited in claim 1, wherein the cylindrical body is an aluminum or aluminum alloy drawn tube obtained through a drawing process.

5. The surface inspection device for a cylindrical body as recited in claim 1, wherein the cylindrical body is a photosensitive drum substrate.

6. The surface inspection device for a cylindrical body as recited in claim 1, wherein the beam splitter is constituted by a half mirror.

7. A surface inspection method for a cylindrical body in which illumination light emitted from an illumination light source is reflected by a beam splitter and applied coaxially to a surface of the cylindrical body, reflected light reflected by the surface of the cylindrical body transmits through the beam splitter to be recognized by a surface condition recognition device, and the beam splitter is arranged to extend along an entire longitudinal length of the cylindrical body, wherein the method is configured such that the illumination light from the illumination light source is applied from one end side of the cylindrical body in an axial direction of the cylindrical body toward the other end side of the cylindrical body so as to be in parallel to the axial direction, and such that the illumination light is simultaneously applied to the entire longitudinal length of the cylindrical body at one time.

8. The surface inspection method for a cylindrical body as recited in claim 7, further comprising the step of:

rotating the cylindrical body about an axis of the cylindrical body.

9. A coaxial epi-illumination device used for a surface inspection device for a cylindrical body for inspecting a surface condition of the cylindrical body on the reflected light reflected by a surface of the cylindrical body, comprising:

an illumination light source disposed above the cylindrical body; and a beam splitter disposed above the cylindrical body so as to correspond to the illumination light source so that illumination light emitted from the illumination light source is reflected by the beam splitter and applied coaxially to a surface of the cylindrical body, reflected light reflected by the surface of the cylindrical body transmits through the beam splitter, and the beam splitter is arranged to extend along an entire longitudinal length of the cylindrical body, wherein the coaxial epi-illumination device is configured such that the illumination light from the illumination light source is applied from one end side of the cylindrical body in an axial direction of the cylindrical body toward the other end side of the cylindrical body so as to be in parallel to the axial direction, and such that the illumination light is simultaneously applied to the entire longitudinal length of the cylindrical body at one time.

* * * * *